United States Patent [19]

Alivo, Jr.

[11] Patent Number: 4,479,648
[45] Date of Patent: Oct. 30, 1984

[54] BOWLERS WRIST BRACE

[76] Inventor: Martin J. Alivo, Jr., 8118 Brentwood Ave., Milwaukee, Wis. 53223

[21] Appl. No.: 385,578

[22] Filed: Jun. 7, 1982

[51] Int. Cl.³ ............................................. A63B 71/14
[52] U.S. Cl. .................................. 273/54 B; 2/161 A; 128/90
[58] Field of Search .......................... 273/54 B, 189 A; 2/161 A; 128/87 R, 89 R, 90; D21/233, 234; D24/64

[56] References Cited

U.S. PATENT DOCUMENTS

| D. 234,434 | 3/1975 | Trevino | 273/189 A X |
|---|---|---|---|
| 239,143 | 3/1976 | Arluck et al. | D24/64 |
| 239,220 | 3/1976 | Norman | 273/54 B |
| 245,429 | 8/1977 | Arluck | 273/54 B X |
| 255,603 | 6/1980 | Finnieston | 128/90 X |
| 2,800,129 | 7/1957 | Van Swaay | 128/90 |
| 3,117,786 | 1/1964 | Anderson | 273/54 B |
| 3,269,728 | 8/1966 | Blough | 273/54 B |
| 3,788,307 | 1/1974 | Kistner | 273/54 B X |
| 3,790,168 | 2/1974 | Hashimoto | 273/54 B |
| 4,040,632 | 8/1977 | Pawl | 273/54 B |
| 4,047,250 | 9/1977 | Norman | 273/54 B |
| 4,143,655 | 3/1979 | Custer et al. | 128/90 |
| 4,228,548 | 10/1980 | Cohen | 273/54 B |

Primary Examiner—Anton O. Oechsle
Attorney, Agent, or Firm—Andrus, Sceales, Starke & Sawall

[57] ABSTRACT

A wrist brace for use by bowlers to prevent movement of the hand relative to the wrist and forearm includes an elongated channel like member formed from low temperature thermoformed plastic and having a hand portion with a palm piece and back hand piece joined by a side piece disposed along the side of the hand opposite the thumb. A wrist portion connects the hand portion to a lower forearm portion and includes a hole disposed opposite the channel opening and surrounding the protrusion of the wrist bone to provide comfort for the wearer of the wrist brace. A plurality of straps span the opening of the channel and secure the wrist brace to the wearer's hand.

4 Claims, 4 Drawing Figures

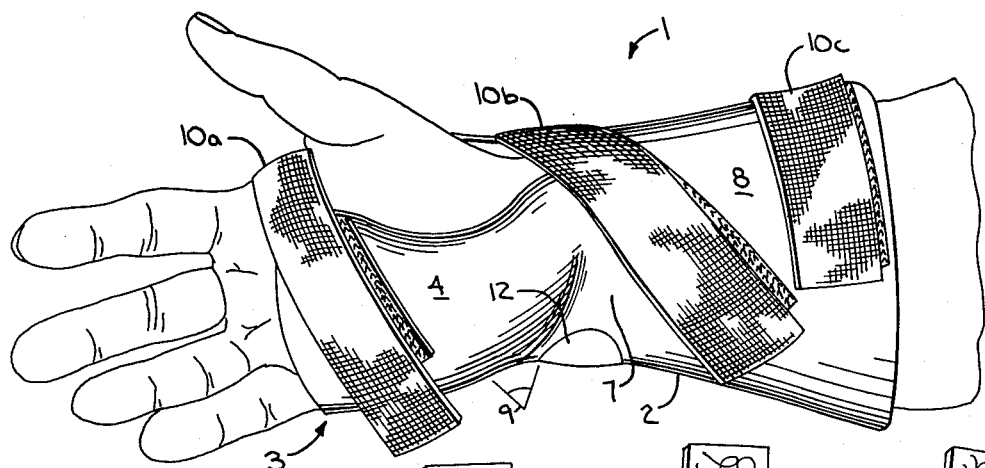
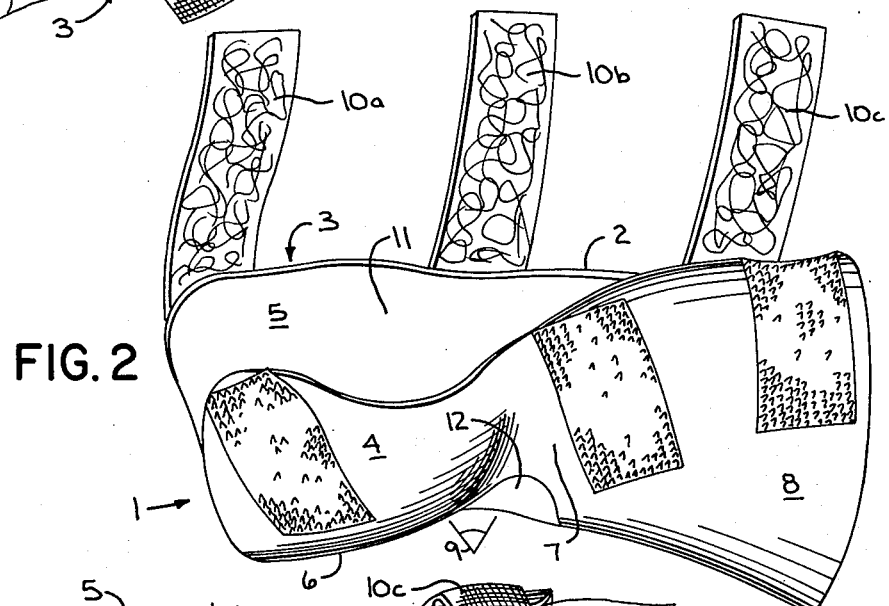
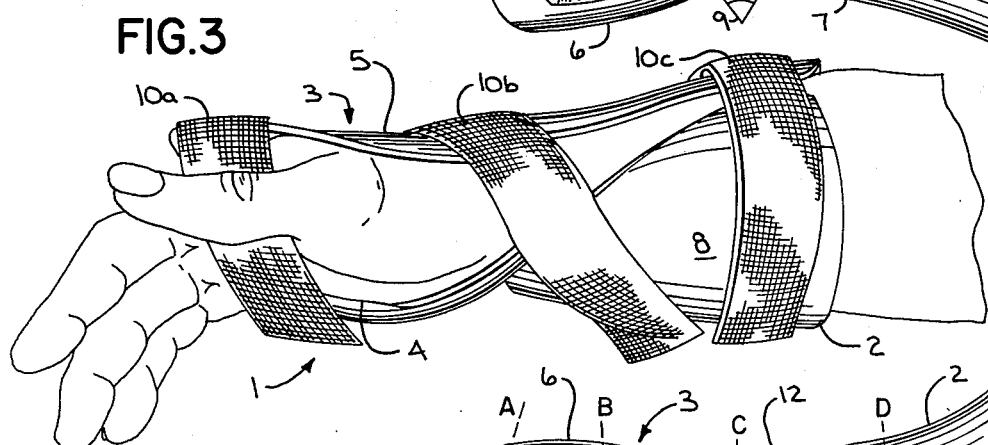
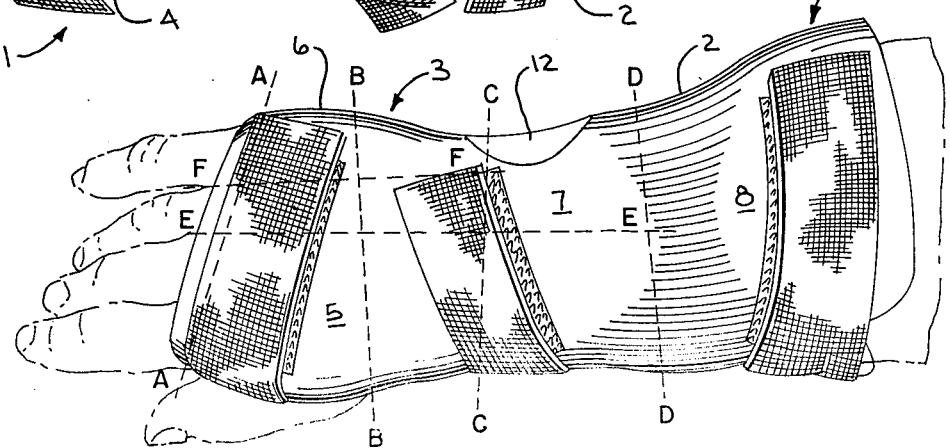

BOWLERS WRIST BRACE

BACKGROUND OF THE INVENTION

The present invention relates to wrist supports and more particularly to wrist braces for use by bowlers.

In order to achieve consistantly high scores in bowling, it is necessary that the bowling ball be properly supported and that the hand and wrist be at the proper position at the point of release so as to deliver the ball with the proper lift and imparted rotation.

The prior art includes the following design patents directed to arm and wrist supports:
U.S. Pat. No. Des. 239,143—Arluck et al;
U.S. Pat. No. Des. 239,220—Norman;
U.S. Pat. No. Des. 245,429—Arluck;
U.S. Pat. No. Des. 255,603—Finnieston.

The prior art also includes the following utility patents:
U.S. Pat. No. 3,117,786—Anderson;
U.S. Pat. No. 3,269,728—Blough;
U.S. Pat. No. 3,790,168—Hashimoto;
U.S. Pat. No. 4,047,250—Norman;
U.S. Pat. No. 4,228,548—Cohen.

A number of these braces or supports are inappropriate for use by a bowler in that they would allow flexing or relative movement between the hand and the wrist. Other prior art devices fail to provide the desired predetermined angle between hand and wrist that is necessary for a proper release of the ball. The prior art wrist braces and supports were also mass produced in a limited number of sizes and thus a proper fit could seldom be guaranteed and a certain amount of play or movement between the hand and the brace was a common result.

SUMMARY OF THE INVENTION

A wrist brace for use by bowlers includes an elongated channel like member formed from low temperature thermoformed plastic. The brace includes a hand portion having a palm piece and a back hand piece joined by a side piece that is disposed along the side of the hand opposite the thumb.

A wrist portion connects the hand portion to a lower forearm portion and the hand portion is connected to the wrist portion at a predetermined angle in order to maintain the proper angle between the hand and the wrist during the delivery of the ball.

A plurality of fastening members span the opening of the channel like member and secure the brace to the wearer's hand.

In accordance with another aspect of the invention, the brace is provided with a hole located substantially opposite the channel opening and surrounding the protrusion of the wrist bone in order to provide comfort for the bowler.

In accordance with yet another aspect of the invention, the wrist brace is custom fit to the bowler's hand, wrist and lower forearm by taking a series of precise measurements along the bowler's hand, wrist and forearm thus guaranteeing a precise fit of brace to hand in order to minimize the amount of play between the bowler's hand and the brace and thus minimize the potential for relative movement between the bowler's hand and wrist.

BRIEF DESCRIPTION OF THE DRAWINGS

The accompanying drawings illustrate the best mode presently contemplated by the inventor for carrying out the invention.

In the drawings:

FIG. 1 is a view of a hand and lower forearm wearing the wrist brace of the present invention with the palm side up;

FIG. 2 is a perspective view of the wrist brace;

FIG. 3 is a side view of a hand and lower forearm wearing the wrist brace with the thumb side up; and FIG. 4 is a view of a hand and lower forearm wearing the wrist brace with the back of the hand facing upwardly.

DESCRIPTION OF THE PREFERRED EMBODIMENT

FIG. 1 illustrates the preferred embodiment of a wrist brace 1 to be worn on a bowler's hand, wrist and lower forearm. Brace 1 includes a one piece channel like member 2 that is formed from a low temperature thermoformed plastic resulting in a rigid and substantially inflexible device.

Brace 1 includes a hand portion 3 that is comprised of a palm piece 4 and a back hand piece 5 that are joined by a side piece 6 which runs along the side of the wearer's hand opposite that of the thumb. Palm piece 4 engages substantially all of the wearer's palm so that only the palm portion at the base of the wearer's thumb is exposed, the palm piece being curved slightly inwardly toward the palm in order to follow the natural contour of the palm and thus eliminate any play or room for movement between the hand and hand portion 3.

Hand portion 3 is integrally joined to wrist portion 7 which in turn is integrally formed with lower forearm portion 8. The wrist and forearm portions engage substantially all of the wearer's wrist and lower forearm. When forming brace 1 from the thermoformed plastic, hand portion 3 is set at a predetermined angle 9 to wrist portion 7. This enables the brace to maintain the hand at the desired angle to the wrist during the delivery of the ball and specifically at the point of release.

A series of VELCRO ® straps 10a–10c are provided for securing wrist brace 1 to the hand of the bowler. Each of straps 10a–10c span the opening 11 in channel like member 2. Strap 10a spans opening 11 substantially between the thumb and index finger of the bowler. Strap 10b spans the opening substantially at wrist portion 7 and strap 10c spans the opening substantially at the outer end of lower forearm portion 8.

Wrist portion 7 is provided with a hole 12 located substantially opposite opening 11 in channel like member 2. Hole 12 provides an opening in brace 1 for the wrist bone of the bowler and greatly adds to the comfort of brace 1.

In order to provide a secure and custom fit of brace 1 to the bowler's hand, a series of measurements are taken along different lines of the bowler's hand prior to the casting or forming of brace 1.

The circumference of the hand is first measured along line A—A which runs along the knuckles at the base of the fingers. The circumference of the widest part of the hand along line B—B which runs under the base of the thumb is then measured. The circumference of the wrist and lower forearm is then measured along lines C—C and D—D, respectively. Finally, two straight line measurements are taken along line E—E which runs from the base of the middle finger to a point approximately three inches above the wrist and along line F—F which runs from a point between the little finger and the ring finger to the wrist bone of the bowler.

The taking of these measurements insures that there will be no gaps or play between brace 1 and the hand, wrist and lower forearm of the bowler and thus the hand is locked into a predetermined position relative to the wrist and forearm by brace 1 and movement of the hand relative to the wrist is eliminated.

Various modes for carrying out the invention are contemplated as being within the scope of the following claims particularly pointing out and distinctly claiming the subject matter which is regarded as the invention.

I claim:

1. A wrist brace for use by bowlers to prevent rotational movement of the hand about the wrist joint comprising
   an elongated channel shaped rigid member custom shaped to precisely fit the contours of the wearer's hand, wrist and lower forearm, said elongated member consisting of
   a hand portion having a rigid palm piece engaging substantially all of the wearer's palm so that only the palm portion at the base of the wearer's thumb is exposed, said palm piece being curved slightly inwardly toward the palm in order to follow the natural contour of the hand and eliminate any play or room for movement between the hand and said hand portion, and a rigid backhand piece joined by a rigid side piece, said side piece disposed along the side of the hand opposite the thumb so as to allow the area between the thumb and the index finger to remain substantially unobstructed,
   a rigid wrist portion connecting said hand portion to a rigid lower forearm portion, said rigid wrist and forearm portions engaging substantially all of the wearer's wrist and lower forearm, said hand portion connected to said wrist portion at a predetermined angle enabling said brace to maintain the hand at the desired said angle to the wrist during delivery of the ball and specifically at the point of release, said palm piece cooperating with said forearm portion to prevent rotational movement of the hand about the wrist joint, and
   a plurality of fastening members spanning the opening of said channel shaped member and securing said member to the wearer's hand.

2. The wrist brace defined in claim 1 wherein said wrist portion includes a hole disposed substantially opposite said channel opening, said hole surrounding the protrusion of the wrist bone to provide comfort for the wearer.

3. The wrist brace defined in claim 1 wherein said plurality of fastening members comprises at least three straps with a first strap spanning said channel substantially between the thumb and the index finger, in a way as to still allow the thumb to lay flat along the index finger, a second strap spanning said channel substantially at said wrist portion and a third strap spanning said channel substantially at the outer end of said lower forearm portion.

4. A wrist brace for use by bowlers to prevent movement of the hand about the wrist joint comprising
   an elongated channel shaped rigid member custom shaped to precisely fit the contours of the wearer's hand, wrist and lower forearm, said elongated member consisting of
   a hand portion having a rigid palm piece engaging substantially all of the wearer's palm so that only the palm portion at the base of the wearer's thumb is exposed, said palm piece being curved slightly inwardly toward the palm in order to follow the natural contour of the hand and eliminate any play or room for movement between the hand and said hand portion, and a rigid backhand piece joined by a rigid side piece, said side piece disposed along the side of the hand opposite the thumb so as to allow the area between the thumb and the index finger to remain substantially unobstructed,
   a rigid wrist portion connecting said hand portion to a rigid lower forearm portion, said rigid wrist and forearm portions engaging substantially all of the wearer's wrist and lower forearm, said hand portion connected to said wrist portion at a predetermined angle enabling said brace to maintain the hand at the desired said angle to the wrist during delivery of the ball and specifically at the point of release, said palm piece cooperating with said forearm portion to prevent rotational movement of the hand about the wrist joint,
   said wrist portion having a hole disposed substantially opposite said channel opening, said hole surrounding the protrusion of the wrist bone to provide comfort for the wearer, and
   a plurality of fastening members spanning the opening of said channel shaped member and securing said member to the wearer's hand.

* * * * *